United States Patent
Rezach et al.

(10) Patent No.: US 10,561,453 B2
(45) Date of Patent: Feb. 18, 2020

(54) BONE FASTENER AND METHODS OF USE

(71) Applicant: Warsaw Orthopedic, Inc., Warsaw, IN (US)

(72) Inventors: William Alan Rezach, Atoka, TN (US); Christopher M. Patterson, Olive Branch, MS (US); Michelle M. Hennard, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 870 days.

(21) Appl. No.: 14/645,205

(22) Filed: Mar. 11, 2015

(65) Prior Publication Data
US 2016/0262817 A1 Sep. 15, 2016

(51) Int. Cl.
*A61B 17/86* (2006.01)

(52) U.S. Cl.
CPC .................. *A61B 17/8605* (2013.01)

(58) Field of Classification Search
CPC .............. A61F 17/7032; A61F 17/7035; A61F 17/7037; A61B 17/7032; A61B 17/7035; A61B 17/7037
See application file for complete search history.

(56) References Cited

U.S. PATENT DOCUMENTS

| | | | | |
|---|---|---|---|---|
| 5,681,319 A | * | 10/1997 | Biedermann | A61B 17/7032 606/104 |
| 6,280,442 B1 | * | 8/2001 | Barker | A61B 17/7037 606/256 |
| 2010/0023063 A1 | * | 1/2010 | Densford | A61B 17/7032 606/308 |
| 2010/0087873 A1 | * | 4/2010 | Null | A61B 17/7034 606/306 |

* cited by examiner

*Primary Examiner* — Christopher D. Prone (57) ABSTRACT

A bone fastener includes a proximal portion including an inner surface defining an implant cavity. A first member is configured for disposal with the proximal portion and includes a wall defining a cavity. A second member is configured for disposal with the cavity. A distal portion includes a first end disposed within the members and a second end configured to penetrate tissue. The proximal portion overlaps the second member to limit movement of the first end of the distal portion. Systems and methods are disclosed.

19 Claims, 8 Drawing Sheets

BONE FASTENER AND METHODS OF USE

TECHNICAL FIELD

The present disclosure generally relates to medical devices for the treatment of spinal disorders, and more particularly to a surgical implant system including a bone fastener that provides stabilization while reducing stress on spinal elements.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, a bone fastener is provided. The bone fastener includes a proximal portion including an inner surface defining an implant cavity. A first member is configured for disposal with the proximal portion and includes a wall defining a cavity. A second member is configured for disposal with the cavity. A distal portion includes a first end disposed within the members and a second end configured to penetrate tissue. The proximal portion overlaps the second member to limit movement of the first end of the distal portion. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a spinal implant system including a bone fastener. In one embodiment, the surgical system includes a screw assembly that includes an insert that lightly loads a ball joint of a bone fastener to limit ball joint movement. This configuration allows a surgeon to position the head of the bone fastener and have it retain that position. In one embodiment, the surgical system includes a multi-axial screw that includes a compressible insert. In one embodiment, the insert can be wrapped around a crown or inserted into pockets of the crown. In one embodiment, the insert can be fabricated from silicone with a durometer range of 40-80.

In one embodiment, the surgical system includes a bone fastener that comprises a multi-axial screw compression element or insert. In one embodiment, the surgical system includes a bone fastener including a compression insert and a ball joint that is lightly loaded to limit movement of the ball joint. In one embodiment, the compression insert is configured to compress to facilitate implant assembly. In one embodiment, the bone fastener includes an insert comprising a bumper. In one embodiment, the bumper is fabricated from silicone, as described herein. In one embodiment, the bumper maintains the components stationary. In one embodiment, the bumper does not contact the shaft of the bone screw. In one embodiment, the bumper is configured for assembly with a standard 5.5/6.0 geometry construct. In one embodiment, the bumper is inserted with a head and/or receiver of a bone screw such that the bumper is captured relative to a crown of the bone screw assembly. In one embodiment, the bumper includes a triangular configuration. In one embodiment, the bumper includes a circular configuration.

In one embodiment, the screw assembly includes a crown having a cut-out or pocket that receives a compressible insert, as described herein. In one embodiment, the crown can be fabricated from silicone with a durometer range of 40-80. In one embodiment, a head or receiver of the screw assembly overlaps the insert to indicate compression and preload to the ball joint of the screw assembly.

In one embodiment, the insert is compressible and has a symmetric design that resists and/or prevents accidental or assembly error. In one embodiment, the insert includes a cutout that is disposed in a lower half of the crown. In some embodiments, the cutout can extend into a top portion of the crown. In some embodiments, the cutout is triangular and disposed with the lower half of the crown as it is retained in a vertical direction. In some embodiments, the cutout is circular and extends into a top portion of the crown as the lower half does not extend past the horizon and retains in a vertical direction. In one embodiment, the insert comprises a sleeve that is wrapped about a crown of the screw assembly.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-5, there are illustrated components of a spinal implant system 30 including a bone fastener 32 in accordance with the principles of the present disclosure.

The components of spinal implant system 30 can be fabricated from biologically acceptable materials suitable for medical applications, including metals, synthetic polymers, ceramics and bone material and/or their composites, depending on the particular application and/or preference of a medical practitioner. For example, the components of spinal implant system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 30 may have material composites, including the above materials, to achieve various desired characteristics such as strength, rigidity, elasticity, compliance, biomechanical performance, durability and radiolucency or imaging preference. The components of spinal implant system 30, individually or collectively, may also be fabricated from a heterogeneous material such as a combination of two or more of the above-described materials. The components of spinal implant system 30 may be monolithically formed, integrally connected or include fastening elements and/or instruments, as described herein.

Figure 1:
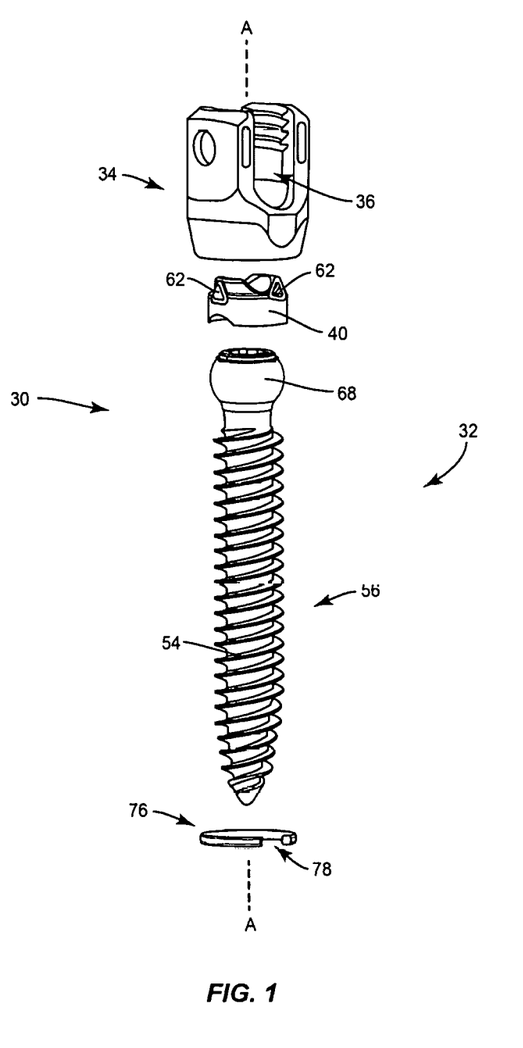
FIG. 1 is a perspective view of components of one embodiment of a spinal implant system in accordance with the principles of the present disclosure.

Fastener 32 includes a proximal portion, such as, for example, a receiver 34 extending along an axis A. Receiver 34 includes a pair of spaced apart arms. Inner surfaces of the arms define an implant cavity 36 configured for disposal of a spinal construct, such as, for example, a spinal rod. The arms each extend parallel to axis A, as shown in FIG. 1. In some embodiments, at least one of the arms may be disposed at alternate orientations, relative to axis A, such as, for example, transverse, perpendicular and/or other angular orientations such as acute or obtuse, coaxial and/or may be offset or staggered. In other embodiments, the tops of the arms may be attached together such that the implant cavity is closed. Thus, the receiver may be an open or closed top-loading configuration, open or closed side-loading configuration or other configurations of a receiver. The arms each include an arcuate outer surface extending between a pair of side surfaces. At least one of the outer surfaces and the side surfaces of the arms have at least one recess or cavity therein configured to receive an insertion tool, compression instrument and/or instruments for inserting and tensioning fastener 32.

Cavity 36 is substantially U-shaped. In some embodiments, all or only a portion of cavity 36 may have alternate cross section configurations, such as, for example, V-shaped, W-shaped, oval, oblong triangular, square, polygonal, irregular, uniform, non-uniform, offset, staggered, and/or tapered. The inner surfaces of the arms each include a thread form. The thread forms are each configured for engagement with a coupling member, such as, for example, a setscrew, to retain a spinal construct, such as, for example, a spinal rod within cavity 36. In some embodiments, receiver 34 may be disposed with the coupling member in alternate fixation configurations, such as, for example, friction fit, pressure fit, locking protrusion/recess, locking keyway and/or adhesive. In some embodiments, all or only a portion of receiver 34 may have alternate surface configurations to enhance engagement with the spinal rod and/or the setscrew such as, for example, rough, arcuate, undulating, mesh, porous, semi-porous, dimpled and/or textured.

Figure 2:
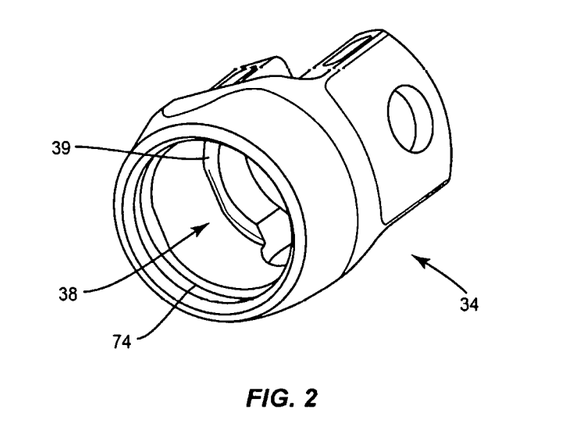
FIG. 2 is a perspective view of components shown in FIG. 1.
Figure 3:
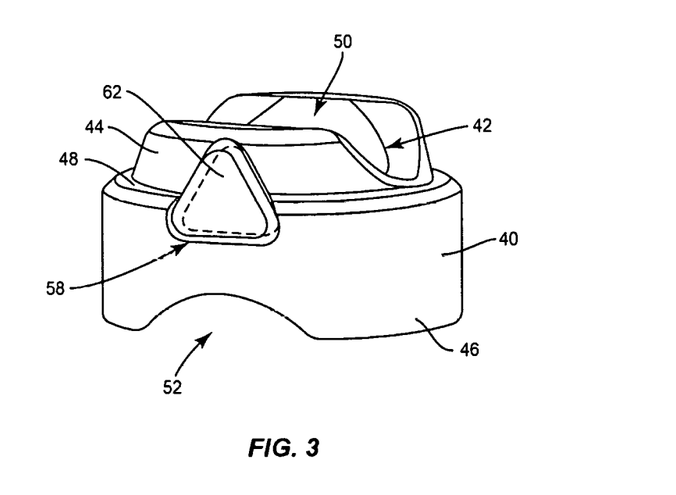
FIG. 3 is a perspective view of components shown in FIG. 1.
Figure 4:
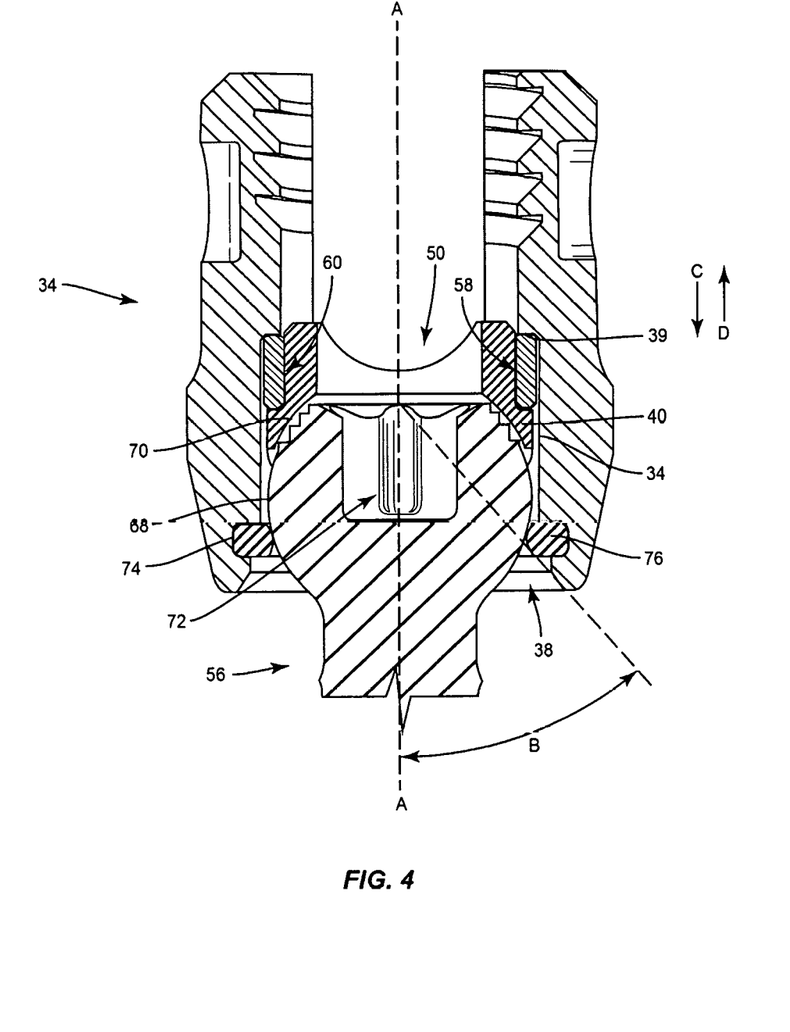
FIG. 4 is a break away cross section view of components shown in FIG. 1
Figure 5:
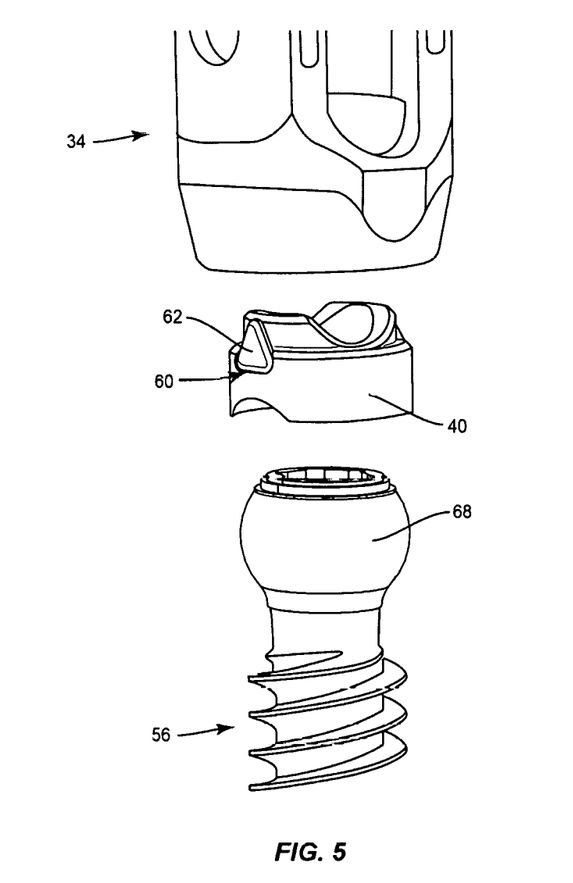
FIG. 5 is a break away view of components shown in FIG. 1.

An inner wall 37 of receiver 34 and a transverse wall 39 of receiver 34 define an aperture 38, as shown in FIG. 2, configured for disposal of a member, such as, for example, a crown 40. Wall 37 is spaced apart from an outer surface 66 of crown 40 when crown 40 is disposed in aperture 38, as shown in FIG. 4. An upper surface of crown 40 defines a channel 42 configured for disposal of a spinal construct, such as, for example, a spinal rod. Channel 42 is substantially U-shaped. In some embodiments, all or only a portion of channel 42 may have alternate cross section configurations, such as, for example, V-shaped, W-shaped, oval, oblong triangular, square, polygonal, irregular, uniform, non-uniform, offset, staggered, and/or tapered. In some embodiments, channel 42 extends parallel to cavity 36 such that a spinal construct, such as, for example, a spinal rod may be top-loaded into cavity 36 and subsequently positioned for disposal in channel 42 without rotating crown 40 relative to receiver 34. In some embodiments, wall 39 may be disposed at alternate orientations, relative to axis A, such as, for example, transverse, perpendicular and/or other angular orientations such as acute or obtuse, co-axial and/or may be offset or staggered. In some embodiments, wall 39 is proximal relative to a bottom portion of cavity 36, as shown in FIG. 2. In some embodiments, wall 39 includes a first portion adjacent one of the arms and a second portion adjacent the other arm, there being gaps between the first and second portions, the gaps being aligned with cavity 36. In some embodiments, wall 39 extends circumferentially about axis A so as to define a circular ring without any gaps.

Figure 6:
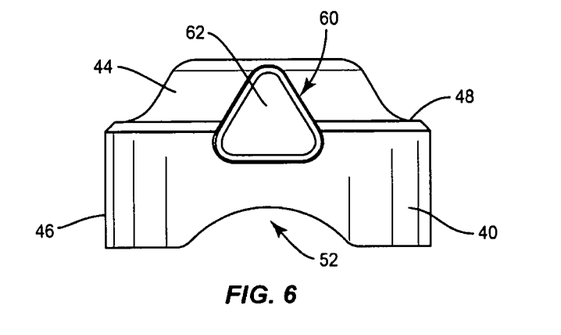
FIG. 6 is a side view of a component of one embodiment of a spinal implant system in accordance with the principles of the present disclosure.
Figure 7:
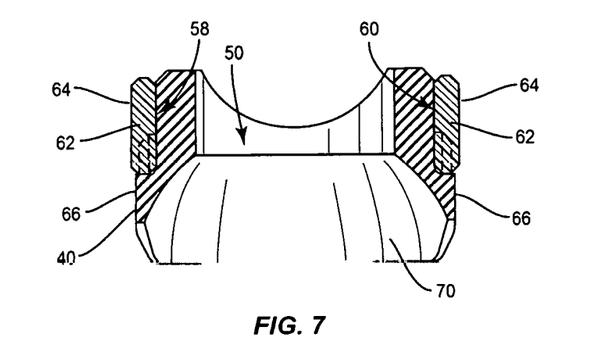
FIG. 7 is a cross section view of the component shown in FIG. 6.
Figure 8:
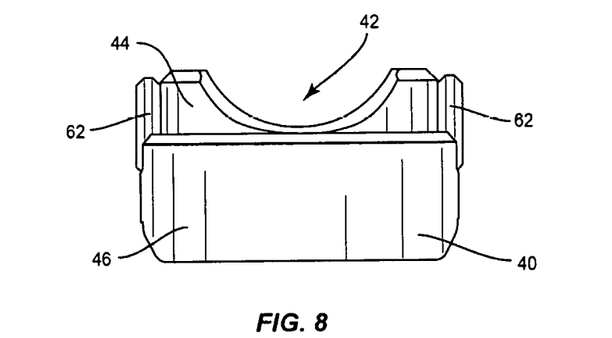
FIG. 8 is a side view of the component shown in FIG. 6.

Crown 40 includes an upper portion 44 and a lower portion 46, as shown in FIGS. 6-8. Portion 44 has a first maximum diameter and portion 46 has a second maximum diameter that is greater than the first maximum diameter. An interface between portions 44, 46 defines a flange 48 extending transverse to axis A. In some embodiments, flange 48 extends perpendicular to axis A. A throughhole 50 extends through opposite top and bottom surfaces of crown 40. Portion 46 defines a side cavity 52 in communication with throughhole 50 and configured for moveable disposal of a threaded shaft 54 of a distal portion, such as for example, a bone anchor 56 when shaft 54 is rotated relative to receiver 34. Cavity 52 is concavely curved between a first end and a second end. In some embodiments, cavity 52 may be variously configured and dimensioned, such as, for example, convex, polygonal, irregular, uniform, non-uniform, staggered, tapered, consistent or variable.

Crown 40 includes a cavity, such as, for example, a pocket 58 extending into outer surfaces of portions 44, 46 at a first side of crown 40 and a cavity, such as, for example, a pocket 60 extending into outer surfaces of portions 44, 46 at an opposite second side such that pocket 58 is positioned opposite pocket 60. In some embodiments, pocket 58 is identical to pocket 60. In some embodiments, pocket 58 has a different configuration than pocket 60 with regard to size and/or shape. In some embodiments, at least one of pockets 58, 60 is positioned in portion 46 without extending into portion 44. In some embodiments, at least one of pockets 58, 60 is positioned in portion 44 without extending into portion 46. In some embodiments, crown 40 includes one or a plurality of pockets 58 and/or pockets 60.

Pockets 58, 60 each include a member, such as, for example, a compression insert 62 disposed therein. In some embodiments, inserts 62 are each formed from a compressible material, such as, for example, silicone. In some embodiments, at least one of inserts 62 is fabricated from a pliable, compressible and/or deformable material, such as, for example, silicone, polyurethane, silicone-polyurethane copolymers, polymeric rubbers, polyolefin rubbers, elastomers, rubbers, thermoplastic elastomers, thermoset elastomers and elastomeric composites. In some embodiments, inserts 62 each comprise a material having a durometer range of about 40 A to about 80 A. In some embodiments, inserts 62 are each formed from the same material(s). In some embodiments, inserts 62 are formed from different materials.

In some embodiments, pockets 58, 60 have a configuration that accommodates inserts 62. In some embodiments, inserts 62 and pockets 58, 60 each have a triangular configuration. In some embodiments, inserts 62 and pockets 58, 60 each have a circular configuration. In some embodiments, inserts 62 are removably disposed in pockets 58, 60. In some embodiments, at least one of inserts 62 and pockets 58, 60 may have various surface configurations, such as, for example, smooth and/or surface configurations to enhance fixation with at least one of inserts 62 and pockets 58, 60, such as, for example, rough, arcuate, undulating, porous, semi-porous, dimpled, polished and/or textured. In some embodiments, inserts 62 can be variously connected with pockets 58, 60, such as, for example, monolithic, integral connection, frictional engagement or adhesive. In some embodiments, inserts 62 completely fill pockets 58, 60. In some embodiments, inserts 62 fill substantially all of pockets 58, 60. In some embodiments, at least one of inserts 62 has a height that is greater than a depth of at least one of pockets 58, 60 such that an outer surface 64 of at least one of inserts 62 extends beyond an outer surface 66 of crown 40 and/or is proud relative to surface 66, as shown in FIG. 7. This configuration allows surfaces 64 to engage wall 37 when crown 40 and inserts 62 are disposed in aperture 38 such that surface 66 is spaced apart from wall 37, as shown in FIG. 2. Top surfaces of inserts 62 engage wall 39 when crown 40 and inserts 62 are disposed in aperture 38 to fix inserts 62 relative to crown 40.

Shaft 54 is configured to penetrate tissue, such as, for example, bone. Anchor 56 includes a rounded head 68 disposed within aperture 38, as shown in FIG. 4. Head 68 is substantially spherical and is configured for engagement with crown 40 and moveable disposal within aperture 38. Head 68 includes a plurality of ridges to improve purchase of head 68 with crown 40. A lower surface 70 of portion 46 is concave or semi-spherical to accommodate the substantially spherical configuration of head 68 such that shaft 54 is rotatable relative to receiver 34 about axis A in a caudal or cephalad orientation in a range of 0-180 degrees.

Shaft 54 is movable relative to receiver 34 between a first orientation in which shaft 54 is coaxial with axis A and a second orientation in which shaft 54 extends through an angular range, for example angular range B, of greater than 0 degrees through about 45 degrees relative to axis A, as shown in FIG. 4. In some embodiments, in the second orientation, at least a portion of shaft 54 is disposed in cavity 52. In one embodiment, shaft 54 is rotatable to a selected angle through and within angular range B relative to axis A, as shown in FIG. 4. In some embodiments, shaft 54 is rotatable in a plurality of planes that lie in a cone configuration about receiver 34 that defines a range of motion of shaft 54 about axis A. In one embodiment, shaft 54 is rotatable to a selected angle within angular range B in a sagittal plane of a body of a patient. In one embodiment, shaft 54 is rotatable to a selected angle within angular range B in a transverse plane of the body. In one embodiment, shaft 54 is rotatable to a selected angle within angular range B in a coronal plane of the body.

Head 68 includes a socket 72 having a hexalobe geometry configured for disposal of a similarly shaped bit of a tool, such as, for example, a driver to engage the driver with anchor 56 to rotate shaft 54 clockwise or counterclockwise relative to axis A. Socket 72 is in communication with throughhole 50 such that a driver may be inserted between the arms of receiver 34, into cavity 36, and translated axially, in the direction shown by arrow C, until the bit of the driver is disposed in socket 72. In some embodiments, socket 72 has a cruciform, phillips, square, hexagonal, polygonal, star or hexalobe cross sectional configuration configured for disposal of a correspondingly shaped portion of a driver.

Receiver 34 includes a groove 74, as shown in FIG. 2, extending into wall 37, in a direction transverse to axis A. Groove 74 includes a concave or semi-cylindrical configuration for disposal of a third member, such as, for example, a compressible snap ring 76 to maintain head 68 within aperture 38. In some embodiments, groove 74 may be disposed at alternate orientations, relative to axis A, such as, for example, perpendicular and/or other angular orientations such as acute or obtuse, coaxial and/or may be offset or staggered. In some embodiments, all or only a portion of groove 74 may have various surface configurations, such as, for example, rough, arcuate, undulating, porous, semi-porous, dimpled, polished and/or textured, to enhance engagement of groove 74 with ring 76.

Ring 76 includes a C-shaped band portion extending between a first end and a second end. The first and second ends of ring 76 are spaced apart by an opening 78, as shown in FIG. 1. Ring 76 is configured to surround a portion of anchor 56 and is disposable with groove 74 to prevent axial translation of head 68 relative to receiver 34, in the direction shown by arrow C. Opening 78 is aligned with cavity 52 when ring 76 engages an outer surface of shaft 54 to permit shaft 54 to be moveably disposed within cavity 52 and aperture 38 such that a distal end of shaft 54 is disposed in a range of greater than 0 degrees through 45 degrees relative to axis A. In some embodiments, groove 74 and/or ring 76 may have alternate cross section configurations, such as, for example, oval, oblong, triangular, square, hexagonal, polygonal, irregular, uniform, non-uniform and/or tapered.

In one embodiment, the components of fastener 32 are assembled. At least one of inserts 62 is positioned in at least one of pockets 58, 60. Crown 40 is positioned distal to aperture 38 with channel 42 aligned with cavity 36 such that channel 42 extends parallel to cavity 36. Crown 40 is translated axially, in the direction shown by arrow D, until top surfaces of inserts 62 engage wall 39 and surfaces 64 engage wall 37, as shown in FIG. 4. Head 68 is positioned in aperture 38 and translated axially, in the direction shown by arrow D, such that head 68 engages surface 70. Ring 76 is positioned about shaft 54 with opening 78 aligned with cavity 52. Ring 76 is disposed with groove 74, as shown in FIG. 4, to maintain head 68 within aperture 38 such that surface 70 and head 68 define a ball joint. Inserts 62 engage receiver 34 to load the ball joint in a manner that limits ball joint movement. This configuration results in receiver 34 overlapping inserts 62 to limit movement of head 68, which allows a medical practitioner to position receiver 34 in a selected orientation relative to shaft 54, and maintain receiver 34 in the selected orientation.

Figure 9:
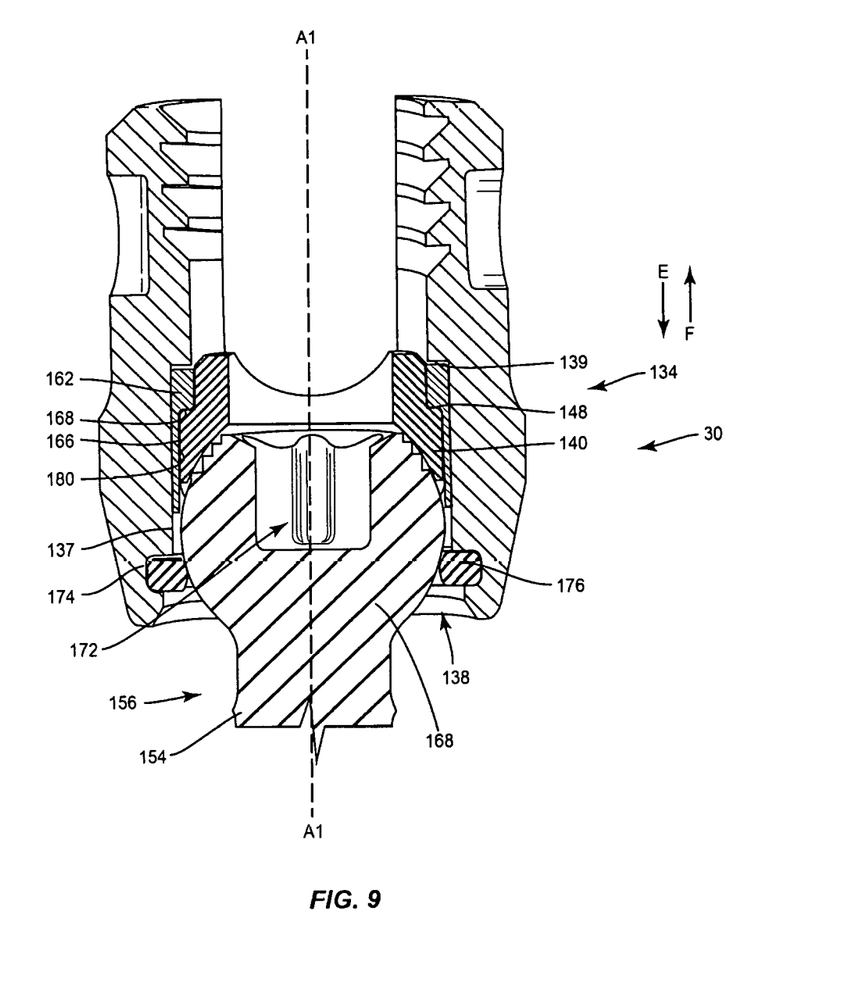
FIG. 9 is a break away cross section view of components of one embodiment of a spinal implant system in accordance with the principles of the present disclosure.
Figure 10:
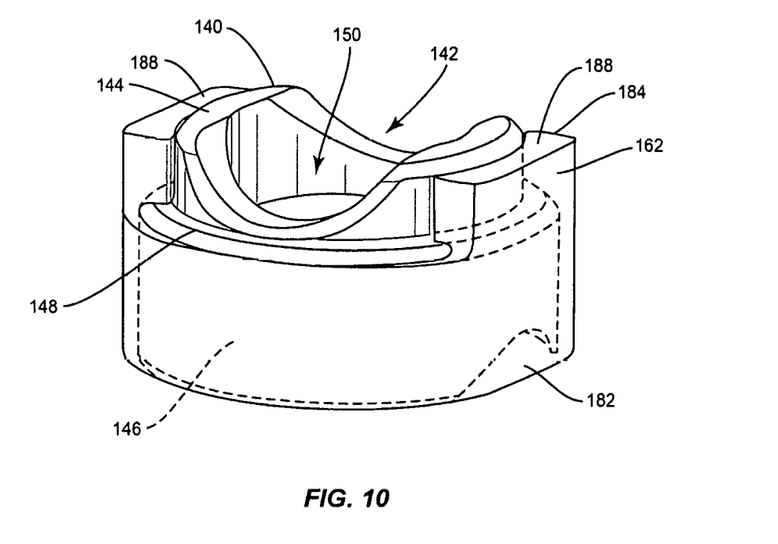
FIG. 10 is a perspective view of components shown in FIG. 9.

In one embodiment, as shown in FIGS. 9 and 10, system 30, similar to the systems and methods described above with regard to FIGS. 1-8, includes a bone fastener 132, similar to fastener 32. Fastener 132 includes a proximal portion, such as, for example, a receiver 134, similar to receiver 34, extending along an axis A1. Receiver 134 includes a pair of spaced apart arms. Inner surfaces of the arms define an implant cavity 136 configured for disposal of a spinal construct, such as, for example, a spinal rod. The arms each extend parallel to axis A1, as shown in FIG. 9. Cavity 36 is substantially U-shaped.

An inner wall 137 of receiver 134 and a transverse wall 139 define an aperture 138, as shown in FIG. 9, configured for disposal of a member, such as, for example, a crown 140, similar to crown 48. Wall 37 is spaced apart from an outer surface 166 of crown 140 when crown 140 is disposed in aperture 138, as shown in FIG. 9. An upper surface of crown 140 defines a channel 142 configured for disposal of a spinal construct, such as, for example, a spinal rod. Channel 142 is substantially U-shaped. In some embodiments, channel 142 extends parallel to cavity 136 such that a spinal construct, such as, for example, a spinal rod may be top-loaded into cavity 136 and subsequently positioned for disposal in channel 142 without rotating crown 140 relative to receiver 134.

Crown 140 includes an upper portion 144 and a lower portion 146. Portion 144 has a first maximum diameter and portion 146 has a second maximum diameter that is greater than the first maximum diameter. An interface between portions 144, 146 defines a flange 148 extending transverse to axis A1. In some embodiments, flange 148 extends perpendicular to axis A1. A throughhole 150 extends through opposite top and bottom surfaces of crown 140. Portion 146 defines a side cavity 152 in communication with throughhole 150 and configured for moveable disposal of a shaft 154, similar to shaft 54, of a distal portion, such as for example, a bone anchor 156 when shaft 154 is rotated relative to receiver 134. Cavity 152 is concavely curved between a first end and a second end.

An inner surface 180 of a member, such as, for example, a compression sleeve 162 engages surface 166 such that sleeve 162 completely surrounds crown 140, as shown in FIG. 10. Sleeve 162 includes a lower portion 182 that overlaps portion 146 and an upper portion 184 that overlaps portion 144 Portion 182 has a maximum thickness that is less than that of portion 184. An interface between portions 182, 184 defines a lip 186 that engages flange 148 to fix sleeve 162 with crown 140.

In some embodiments, sleeve 162 is formed from a compressible material, such as, for example, silicone. In some embodiments, sleeve 162 is fabricated from a pliable, compressible and/or deformable material, such as, for example, silicone, polyurethane, silicone-polyurethane copolymers, polymeric rubbers, polyolefin rubbers, elastomers, rubbers, thermoplastic elastomers, thermoset elastomers and elastomeric composites. In some embodiments, sleeve 162 comprises a material having a durometer range of about 40 A to about 80 A. In some embodiments, at least one of surface 180 and surface 166 may have various surface configurations, such as, for example, smooth and/or surface configurations to enhance fixation between sleeve 162 and crown 140, such as, for example, rough, arcuate, undulating, porous, semi-porous, dimpled, polished and/or textured. In some embodiments, sleeve 162 can be variously connected with crown 140, such as, for example, monolithic, integral connection, frictional engagement or adhesive. A top surface of sleeve 162 engages wall 139 when crown 140 and sleeve 162 are disposed in aperture 138 to fix sleeve 162 relative to crown 40.

Shaft 154 configured to penetrate tissue, such as, for example, bone. Anchor 156 includes a rounded head 168 disposed within aperture 138, as shown in FIG. 9. Head 68 is substantially spherical and is configured for engagement with crown 140 and moveable disposal within aperture 138. Head 168 includes a plurality of ridges to improve purchase of head 168 with crown 140. A lower surface 170 of portion 146 is concave or semi-spherical to accommodate the substantially spherical configuration of head 168 such that shaft 154 is rotatable relative to receiver 134 about axis A1 in a caudal or cephalad orientation in a range of 0-180 degrees.

Shaft 154 is movable relative to receiver 134 between a first orientation in which shaft 154 is coaxial with axis A1, as shown in FIG. 9, and a second orientation in which shaft 154 extends in an angular range similar to angular range B, of greater than 0 degrees through about 45 degrees relative to axis A1. In some embodiments, in the second orientation, at least a portion of shaft 154 is disposed in cavity 152. In some embodiments, shaft 154 is rotatable in a plurality of planes that lie in a cone configuration about receiver 134 that defines a range of motion of shaft 154 about axis A1. In one embodiment, shaft 154 is rotatable to a selected angle in a sagittal plane of a body of a patient. In one embodiment, shaft 154 is rotatable to a selected angle in a transverse plane of the body. In one embodiment, shaft 154 is rotatable to a selected angle in a coronal plane of the body, Head 168 includes a socket 172 having a hexalobe geometry configured for disposal of a similarly shaped bit of a tool, such as, for example, a driver to engage the driver with anchor 156 to rotate shaft 154 clockwise or counter-clockwise relative to axis A1. Socket 172 is in communication with throughhole 150 such that a driver may be inserted between the arms of receiver 134, into cavity 136, and translated axially, in the direction shown by arrow E, until the bit of the driver is disposed in socket 272. In some embodiments, socket 172 has a cruciform, phillips, square, hexagonal, polygonal, star or hexalobe cross sectional configuration configured for disposal of a correspondingly shaped portion of a driver.

Receiver 134 includes a groove 174, as shown in FIG. 9, extending into wall 137, in a direction transverse to axis A1 Groove 174 includes a concave or semi-cylindrical configuration for disposal of a third member, such as, for example, a compressible snap ring 176 to maintain head 168 within aperture 138. In some embodiments, groove 174 may be disposed at alternate orientations, relative to axis A1, such as, for example, perpendicular and/or other angular orientations such as acute or obtuse, coaxial and/or may be offset or staggered. In some embodiments, all or only a portion of groove 174 may have various surface configurations, such as, for example, rough, arcuate, undulating, porous, semi-porous, dimpled, polished and/or textured, to enhance engagement of groove 174 with ring 176.

Ring 176 includes a C-shaped band portion extending between a first end and a second end. The first and second ends of ring 76 are spaced apart by an opening similar to opening 78. Ring 176 is configured to surround a portion of anchor 156 and is disposable with groove 174 to prevent axial translation of head 168 relative to receiver 134, in the direction shown by arrow E. The opening in ring 176 is aligned with cavity 152 when ring 176 engages an outer surface of shaft 154 to permit shaft 154 to be moveably disposed within cavity 152 and aperture 138 such that a distal end of shaft 154 is disposed in a range of greater than 0 degrees through 45 degrees relative to axis A1.

In one embodiment, the components of fastener 132 are assembled. Sleeve 162 is positioned about crown 140 such that surface 180 engages surface 166 and lip 186 engages flange 148. Crown 140 is positioned distal to aperture 138 with channel 142 aligned with cavity 136 such that channel 142 extends parallel to cavity 136. Crown 140 is translated axially, in the direction shown by arrow F, until spaced apart top surfaces 188 of sleeve 162 engage wall 139 and an outer surface 190 of sleeve 162 engages wall 137, as shown in FIG. 9. Head 168 is positioned in aperture 138 and translated axially, in the direction shown by arrow F, such that head 168 engages surface 170. Ring 176 is positioned about shaft 154 with the opening in ring 176 aligned with cavity 152. Ring 176 is inserted and/or snapped into groove 174, as shown in FIG. 9, to maintain head 168 within aperture 138 such that surface 170 and head 168 define a ball joint. Sleeve 162 engages receiver 134 to lightly load the ball joint in a manner that limits ball joint movement. This configuration results in receiver 34 overlapping sleeve 162 to limit movement of head 168, which allows a medical practitioner to position receiver 134 in a selected orientation relative to shaft 154, and maintain receiver 134 in the selected orientation.

In assembly, operation and use, spinal implant system 30, similar to the systems and methods described herein, includes fastener 32 and/or bone fastener 132 and is employed with a surgical procedure for treatment of a spinal disorder affecting a section of a spine of a patient, as discussed herein. Spinal implant system 30 is employed with a surgical procedure for treatment of a condition or injury of an affected section of the spine including vertebrae. In one embodiment, spinal implant system 30 includes fasteners 32 and/or 132 attached to vertebrae for a surgical arthrodesis procedure, such as a fusion of the affected section of the spine to facilitate healing and therapeutic treatment.

In use, to treat the affected section of the spine, a medical practitioner obtains access to a surgical site including the vertebrae in any appropriate manner, such as through incision and retraction of tissues. In some embodiments, the components of spinal implant system 30 may be used in any existing surgical method or technique including open surgery, mini-open surgery, minimally invasive surgery including percutaneous surgical implantation, whereby the vertebrae are accessed through a micro-incision, or sleeve that provides a protected passageway to the area. Once access to the surgical site(s) is obtained, the particular surgical procedure is performed for treating the spinal disorder. The components of spinal implant system 30 including fasteners 32 and/or fasteners 132 are employed to augment the surgical treatment. Fasteners 32 and/or fasteners 132 and one or a plurality of spinal implants, such as, for example, vertebral rods can be delivered or implanted as a pre-assembled device or can be assembled in situ. Spinal implant system 30 may be may be completely or partially revised, removed or replaced.

In some embodiments, one or a plurality of fasteners 32 and/or fasteners 132 are fixed in the vertebrae. The spinal rod is positioned in cavities 36 and/or cavities 136. The setscrews are rotated relative to receivers 34 and/or receivers 134 such that thread forms on the setscrews engage the thread forms on the arms of receivers 34 and/or receivers 134. The setscrews are rotated relative to receivers 34 and/or receivers 134 until distal ends of the setscrews engage the spinal rod to fix the spinal rod within cavities 36 and/or cavities 136.

In some embodiments, spinal implant system 30 can include one or more surgical instruments for use with fasteners 32 and/or fasteners 132, such as, for example, drivers, inserters, extenders, reducers, spreaders, distractors, blades, retractors, damps, forceps, elevators and drills, which may be alternately sized and dimensioned, and arranged as a kit.

In some embodiments, spinal implant system 30 includes one or more fasteners for attaching a spinal construct with tissue, as described herein. In some embodiments, the fasteners may be engaged with tissue in various orientations, such as, for example, series, parallel, offset, staggered and/or alternate vertebral levels. In some embodiments, one or more of the fasteners may comprise multi-axial screws, sagittal angulation screws, pedicle screws, facet screws, tissue penetrating screws, conventional screws and/or expanding screws.

In one embodiment, spinal implant system 30 includes an agent, which may be disposed, packed, coated or layered within, on or about the components and/or surfaces of spinal implant system 30. In some embodiments, the agent may include bone growth promoting material, such as, for example, bone graft to enhance fixation of the components and/or surfaces of spinal implant system 30 with vertebrae. In some embodiments, the agent may include one or a plurality of therapeutic agents and/or pharmacological agents for release, including sustained release, to treat, for example, pain, inflammation and degeneration.

Upon completion of a procedure, surgical instruments and/or tools, assemblies and non-implanted components of system 30 are removes and the incision(s) are closed. One or more of the components of system 30 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 30. In some embodiments, system 30 may include one or a plurality of plates, connectors and/or bone fasteners for use with a single vertebral level or a plurality of vertebral levels.

Figure 11:
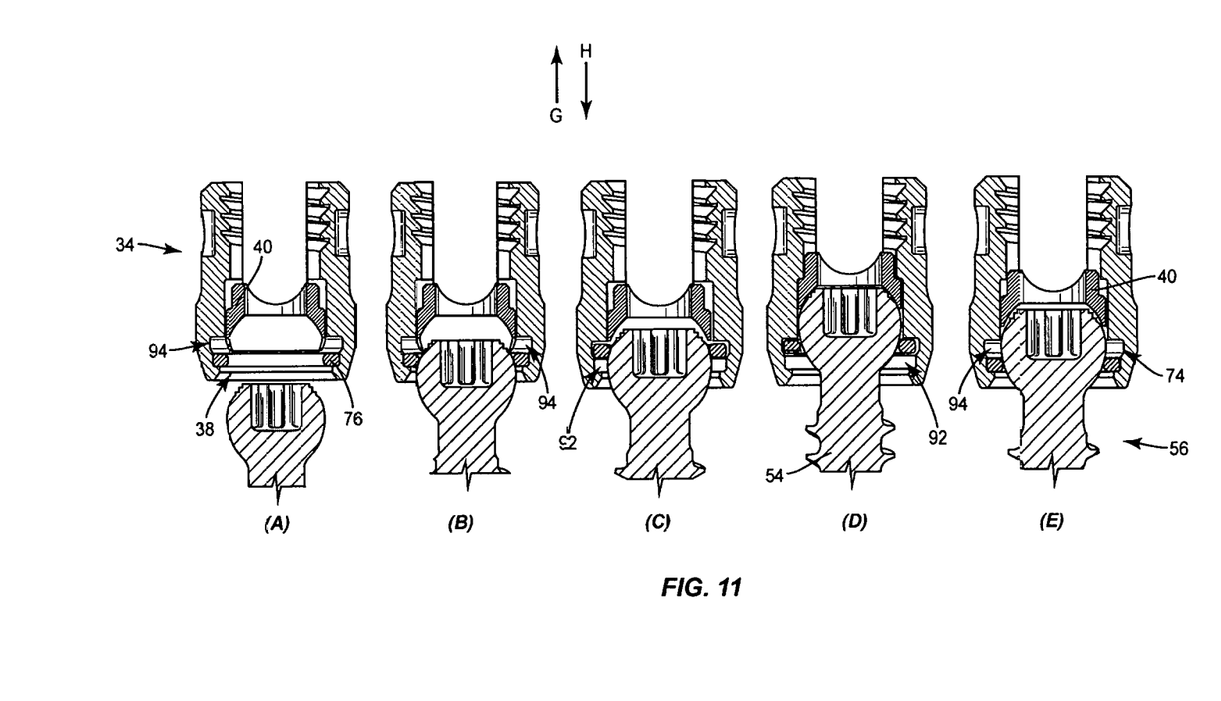
FIG. 11 is a break away cross section view of components of one embodiment of a spinal implant system illustrating assembly.

In one embodiment, as shown in FIG. 11, groove 74 includes a portion 92 having a first diameter and a portion 94 having a second diameter that is greater than the first diameter. Portion 94 is proximal to portion 92. Portions 92, 94 are configured to allow ring 76 to be positioned in groove 74 prior to positioning ring 76 about an outer surface of shaft 54. Ring 76 is positioned in portion 92 with head 68 being spaced apart from aperture 38, as shown in view (A). Head 68 is aligned with aperture 38 and translated axially, in the direction shown by arrow G, until an outer surface of head 68 engages ring 76, as shown in view (B). Head 68 is translated axially, in the direction shown by arrow G, until a diameter of head 68 engages ring 76, causing ring to move from portion 92 and into portion 94, as shown in view (C). The diameter of head 68 is prevented from moving through ring 74 when ring 74 is positioned in portion 92 and is capable of moving through ring 76 when ring 76 is positioned in portion 94. Accordingly, head 68 is translated axially, in the direction shown by arrow G, until the diameter of head 68 is positioned proximal to ring 74, as shown in view (D). This disposes head 68 and/or crown 40 in an up position, as shown in view (D). Anchor 56 is translated axially, in the direction shown by arrow H, causing ring 76 to move from portion 94 and into portion 92, as shown in view (E). This disposes head 68 and/or crown 40 in a down position, as shown in view (E), and permits anchor 56 to be fixed with tissue, such as, for example, bone, prior to engaging anchor 56 with receiver 34.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A fully assembled bone fastener comprising:
 a proximal portion including a transverse surface, and comprising an inner surface defining an implant cavity, the proximal portion including a groove that extends into the inner surface, the inner surface and the transverse surface of the proximal portion defining an aperture;
 a first member comprising an outer surface and being disposed within the proximal portion and including a wall defining a cavity extending into the outer surface;
 a second member having a triangular configuration and comprising an outer surface, the second member being disposed within the cavity of the first member such that the outer surface of the second member directly engages the inner surface of the proximal portion and the outer surface of the first member is spaced apart from the inner surface of the proximal portion;
 a distal portion including a first end disposed within the aperture and a second end configured to penetrate tissue, wherein the proximal portion overlaps the second member to limit movement of the first end of the distal portion; and a third member disposed within the groove such that the first end of the distal portion extends through the third member to maintain the first end within the aperture.

2. The fully assembled bone fastener recited in claim 1, wherein the second member is a compressible insert comprising silicone.

3. The fully assembled bone fastener recited in claim 1, wherein the second member is a compressible insert having a durometer range of about 40 A to about 80 A.

4. The fully assembled bone fastener recited in claim 1, wherein the second member is removable relative to the first member and the proximal portion.

5. The fully assembled bone fastener recited in claim 1 wherein the second member includes an inner surface that engages the outer surface of the first member.

6. The fully assembled bone fastener recited in claim 1, wherein the first member comprises a top portion and the cavity of the first member is positioned in the top portion.

7. The fully assembled bone fastener recited in claim 1, wherein the second member is disposed in the cavity of the first member such that the outer surface of the second member is proud relative to the outer surface of the first member.

8. The fully assembled bone fastener recited in claim 1, wherein the first member includes a second cavity opposite the cavity of the first member, and the bone fastener includes a secondary second member disposed in the second cavity.

9. The fully assembled bone fastener recited in claim 1, wherein the second member is spaced apart from the distal portion.

10. The fully assembled bone fastener recited in claim 1, wherein the outer surface of the first member is spaced apart from the inner surface by the second member.

11. The fully assembled bone fastener recited in claim 1, wherein the first member extends along an axis between an upper portion and a lower portion, the upper portion having a maximum diameter that is less than a maximum diameter of the lower portion, an interference between the portions defining a flange that extends transverse to the axis, the cavity of the first member extending into the flange.

12. The fully assembled bone fastener recited in claim 1, wherein the proximal portion comprises spaced-apart first and second arms, the second arm comprising a thread, the implant cavity being positioned between the arms, the first arm including a thread that faces the thread of the second arm, the threads of the first arm and of the second arm being configured to engage a thread of a set screw to couple the set screw to the proximal portion.

13. A fully assembled bone fastener comprising:

a receiver including spaced-apart first and second arms that define an implant cavity therebetween, the receiver including an inner surface defining an aperture, the first arm including a thread and the second arm including a thread facing the thread of the first arm, the threads of the first arm and the second arm being configured to engage a thread of a set screw to couple the set screw to the receiver;

a crown comprising an outer surface and being positioned within the aperture, the crown including spaced-apart first and second pockets;

a first insert having a triangular configuration, the first insert being positioned in the first pocket;

a second insert having a triangular configuration, the second insert being positioned in the second pocket, wherein outer surfaces of the inserts directly engage the inner surface such that the outer surface of the crown is spaced apart from the inner surface.

14. The fully assembled bone fastener recited in claim 13, wherein the crown extends along an axis between an upper portion and a lower portion, the upper portion having a maximum diameter that is less than a maximum diameter of the lower portion, an interference between the portions defining a flange that extends transverse to the axis, the pockets each extending into the flange.

15. The fully assembled bone fastener recited in claim 13, wherein the crown extends along an axis between an upper portion and a lower portion, the upper portion having a maximum diameter that is less than a maximum diameter of the lower portion.

16. The fully assembled bone fastener recited in claim 13, wherein the crown extends along an axis between an upper portion and a lower portion, the upper portion having a maximum diameter that is less than a maximum diameter of the lower portion, the pockets being positioned in the upper portion and extending into the lower portion.

17. The fully assembled bone fastener recited in claim 11, further comprising a snap ring and a shaft, the shaft having a head, wherein the receiver includes a groove that extends into the inner surface and the snap ring is positioned within the groove such that the head of the shaft of the bone fastener extends through the snap ring to maintain the head in the aperture.

18. The fully assembled bone fastener recited in claim 17, wherein the head is substantially spherical and includes a plurality of ridges to improve purchase of the head by the crown.

19. A fully assembled bone fastener comprising:

a receiver including spaced-apart first and second arms that define an implant cavity therebetween, the receiver including an inner surface defining an aperture, the first arm including a thread and the second arm including a thread facing the thread of the first arm, the threads of the first arm and the second arm being configured to engage a thread of a set screw to couple the set screw to the receiver;

a crown comprising an outer surface and being positioned within the aperture, the crown including spaced-apart first and second pockets;

a first insert having a triangular configuration, the first insert being positioned in the first pocket;

a second insert having a triangular configuration, the second insert being positioned in the second pocket, wherein the crown is spaced apart from the receiver by the inserts.

* * * * *